(12) United States Patent
Rycyzyn et al.

(10) Patent No.: US 7,479,379 B2
(45) Date of Patent: Jan. 20, 2009

(54) METHODS FOR ALTERING PROTEIN PRODUCTION RATES

(75) Inventors: Michael Rycyzyn, Berwyn, PA (US); Gregory Bannish, Morton, PA (US); Jill Giles-Komar, Downingtown, PA (US)

(73) Assignee: Centocor, Inc., Malvern, PA (US)

( * ) Notice: Subject to any disclaimer, the term of this patent is extended or adjusted under 35 U.S.C. 154(b) by 381 days.

(21) Appl. No.: 11/095,893

(22) Filed: Mar. 31, 2005

(65) Prior Publication Data

US 2005/0221432 A1     Oct. 6, 2005

Related U.S. Application Data

(60) Provisional application No. 60/558,239, filed on Mar. 31, 2004.

(51) Int. Cl.
    C12N 15/85     (2006.01)
    C12P 21/06     (2006.01)
(52) U.S. Cl. ..................... 435/69.1; 435/325
(58) Field of Classification Search ............... 435/69.1, 435/325
    See application file for complete search history.

(56) References Cited

U.S. PATENT DOCUMENTS

| | | | |
|---|---|---|---|
| 2001/0034045 | A1 | 10/2001 | Penttila et al. |
| 2004/0170622 | A1 | 9/2004 | Glimcher et al. |
| 2004/0186070 | A1 | 9/2004 | Penttila et al. |
| 2005/0106222 | A1 | 5/2005 | Ailor et al. |

OTHER PUBLICATIONS

Muenier, et al., "A Subset of Chaperones and Folding Enzymes Form Multiprotein Complexes in Endoplasmic Reticulum to Bind Nascent Proteins," *Molecular Biology of the Cell*, 13: 4456-4469 (2002).
Ron, et al., "CHOP, a novel developmentally regulated nuclear protein that dimerizes with transcription factors C/EBP and LAP and functions as a dominant-negative inhibitor of gene transcription," *Genes & Development*, 6: 439-453 (1992).
Shen, et al., "ER Stress Regulation of ATF6 Localization by Dissociation of BiP/GRP78 Binding and Unmasking of Golgi Localization Signals," *Development Cell*, 3:99-111 (2002).
Valkonen, et al., "Effects of Inactivation and Constitutive Expression of the Unfolded-Protein Response Pathway on Protein Production in the Yeast *Saccharomyces cerevisiae*," *Applied and Environmental Microbiology*, 69(4): 2065-2072 (2003).
Haas, et al., "Immunoglobulin heavy chain binding protein," *Nature*, 306; 387-389 (1983).
Kozutsumi, et al., "The presence of malfolded proteins in the endoplasmic reticulum signals the induction of glucose-regulated proteins," *Nature*, 332: 462-464 (1988).
Mori, et al., "A Transmembrane Protein with a cdc2*/CDC28-Related Kinase Activity is Required for Signaling from the ER to the Nucleus," *Cell*, 74: 743-756 (1993).
Cox, et al., "Transcriptional Induction of Genes Encoding Endoplasmic Reticulum Resident Proteins Requires a Transmembrane Protein Kinase," *Cell*, 73: 1197-1206 (1993).
Shamu, et al., "Oligomerization and phosphorylation of the Irelp kinase during intracellular signaling from the endoplasmic reticulum to the nucleus," *EMBO Journal*, 15(12): 3028-3039 (1996).
van Anken, et al., "Sequential Waves of Functionally Related Proteins Are Expressed When B Cells Prepare for Antibody Secretion," *Immunity*. 18: 243-253 (2003).
Wang, et al., "Cloning of mammalian Ire1 reveals diversity in the ER stress responses," *The EMBO Journal*, 17(19): 5708-5717 (1998).
Wang, et al, "Identification of novel stress-induced genes downstream of chop," *The EMBO Journal*, 17(13): 3619-3630 (1998).
Wu, et al., "Ultraviolet Light Inhibits Translation through Activation of the Unfolded Protein Response Kinase PERK in the Lumen of the Endoplasmic Reticulum," *The Journal of Biological Chemistry*, 277(20): 18077-18083 (2002).
Harding, et al., "Regulated Translation Initiation Controls Stress-Induced Gene Expression in Mammalian Cells," *Molecular Cell*, 6: 1099-1108 (2000).
Gass, et al., "Activation of an Unfolded Protein Response during Differentiation of Antibody-secreting B Cells," *The Journal of Biological Chemistry*, 277(50): 49047-49054 (2002).
Fernandez, et al., "Regulation of Internal Ribosomal Entry Site-mediated Translation by Phosphorylation of the Translation Initiation Factor eIF2α," *The Journal of Biological Chemistry*, 277(21): 19198-19205 (2002).
Gülow, et al., "BiP is feed-back regulated by control of protein translation efficiency," *Journal of Cell Science*, 115: 2443-2452 (2002).
Knarr, et al., "Interaction of the Chaperone BiP with an Antibody Domain: Implications for the Chaperone Cycle," *Journal of Molecular Biology*, 318:611-620 (2002).
Ma, et al., "Two Distinct Stress Signaling Pathways Converge Upon the CHOP Promoter During the Mammalian Unfolded Protein Response," *Journal of Molecular Biology*, 318: 1351-1365 (2002).
Harding, et al., "Protein translation and folding are coupled by an endoplasmic-reticulum-resident kinase," *Nature*, 398: 270-274.
Reimold, et al., "Plasma cell differentiation requires the transcription factor XBP-1," *Nature*, 412: 300-307 (2001).
Iwakoshi, et al., Plasma cell differentiation and the unfolded protein response intersect at the transcription factor XBP-1, *Nature: Immunology*, 4(4): 321-329 (2003).
Yoshida, et al., "XBP1 mRNA Is Induced by ATF6 and Spliced by IRE1 in Response to ER Stress to Produce a Highly Active Transcription Factor," *Cell*, 107: 881-891 (2001).
Calame, et al., "Regulatory Mechanisms that Determine the Development and Function of Plasma Cells," *Annual Review of Immunology*, 21: 205-230 (2003).

(Continued)

*Primary Examiner*—Tekchand Saidha
(74) *Attorney, Agent, or Firm*—Kirk Baumeister

(57) ABSTRACT

Methods for altering the cellular secretion rate of a protein, such as an antibody and the altered cells produced by the method are disclosed. The methods and altered cells are useful for producing high levels of proteins for therapeutic, diagnostic or research purposes.

6 Claims, 8 Drawing Sheets

OTHER PUBLICATIONS

Cudna, et al., "Endoplasmic Reticulum Signaling as a Determinant of Recombinant Protein Expression," *Biotechnology and Bioengineering*, 81(1): 56-65 (2003).

Knee, et al., "Compromised calnexin function in calreticulin-deficient cells," *Biochemical and Biophysical Research Communications*, 304: 661-666 (2003).

Lengwehasatit, et al., "Analysis of the Role of GADD153 in the Control of Apoptosis in NS0 Myeloma Cells," *Biotechnology and Bioengineering*, 80(7): 719-730 (2002).

Randal Kaufman, "Stress signaling from the lumen of the endoplasmic reticulum: coordination of gene transcriptional and translational controls," *Genes & Development*, 13: 1211-1233 (1999).

Ubeda, et al., "Stress-Induced Binding of the Transcription Factor CHOP to a Novel DNA Control Element," *Molecular and Cellular Biology*, 16(4): 1479-1489 (1996).

Shi, et al., "Identification and Characterization of Pancreatic Eukaryotic Initiation Factor 2 α-Subunit Kinase, PEK, Involved in Translational Control," *Molecular and Cellular Biology*, 18(12): 7499-7509 (1998).

Lytton, et al., "Thapsigargin Inhibits the Sarcoplasmic or Endoplasmic Reticulum Ca-ATPase Family of Calcium Pumps," *The Journal of Biological Chemistry*, 266(26): 17067-17071 (1991).

Yoshida, et al., "Identification of the *cis*-Acting Endoplasmic Reticulum Stress Response Element Responsible for Transcriptional Induction of Mammalian Glucose-regulated Proteins," *The Journal of Biological Chemistry*, 273(50): 33741-33749 (1998).

Yoshida, et al., "Identification of the *cis*-Acting Endoplasmic Reticulum Stress Response Element Responsible for Transcriptional Induction of Mammalian Glucose-regulated Proteins. Involvement of basic leucine zipper transcription factors," *Erratum in: The Journal of Biological Chemistry*, 273: 2592 (1998).

Calfon, et al., "IRE1 couples endoplasmic reticulum load to secretory capacity by processing the *XBP-1 mRNA*," *Nature*. 415: 92-96 (2002).

Calfon, et al., "IRE1 couples endoplasmic reticulum load to secretory capacity by processing the *XBP-1 mRNA*," *Erratum in: Nature*, 420: 202 (2002).

Wang, et al., "Stress-Induced Phosphorylation and Activation of the Transcription Factor CHOP (GADD153) by p38 MAP Kinase," *Science*, 272: 1347-1349 (1996).

SEQUENCE LISTING

```
<160> NUMBER OF SEQ ID NOS: 16

<210> SEQ ID NO 1
<211> LENGTH: 1965
<212> TYPE: DNA
<213> ORGANISM: Mus musculus

<400> SEQUENCE: 1
atgatgaagt tcactgtggt ggcggcggcg ttgctgctgc tgggcgcggt gcgggccgag      60
gaggaggaca agaaggagga tgtgggcacg gtggtcggca tcgacttggg gaccacctat     120
tcctgcgtcg gtgtgttcaa gaacggccgc gtggagatca tagccaacga tcagggcaac     180
cgcatcacgc cgtcgtatgt ggccttcact cctgaagggg agcgtctgat tggcgatgcg     240
gccaagaacc aactcacgtc caaccccgag aacacggtct tcgatgccaa gcgcctcatc     300
ggacgcactt ggaatgaccc ttcggtgcag caggacatca agttcttgcc attcaaggtg     360
gttgaaaaga aaactaaacc gtacattcaa gttgatattg gaggtgggca aaccaagaca     420
tttgccccag aagaaatttc tgccatggtt ctcactaaaa tgaaggagac tgctgaggcg     480
tatttgggaa agaaggttac ccatgcagtt gttactgtac cagcttactt caatgatgcc     540
cagcgacaag caaccaaaga tgctggcact attgctggac tgaatgtcat gaggatcatc     600
aatgagccta cagcagctgc tattgcatat ggcctggata agagagaggg agagaagaac     660
atccttgtgt ttgacctggg tggcggcacc ttcgatgtgt ctcttctcac cattgacaat     720
ggtgtctttg aagtggtggc cactaatgga gatactcacc tgggtgggga agactttgat     780
cagcgggtca tggaacactt catcaagttg tacaaaaaga aaactggtaa agatgttagg     840
aaagacaaca gagctgtgca gaaactccgg cgtgaggtag aaaaggctaa gagagccttg     900
tcttctcagc atcaagcaag gattgaaatt gagtccttct tcgaaggaga agacttctca     960 gagacccctta ctcgggccaa atttgaagag ctgaacatgg acctgttccg ctctaccatg    1020
aagcctgtcc aggaagtgtt ggaagactct gatctgaaga aatctgatat tgatgaaatt    1080
gttctggttg gtggatctac tcgaattcca aagattcagc aactggtgaa agagttcttc    1140
aatggcaagg agccatcccg tggcataaac cccgatgagg ctgtagccta tggtgccgct    1200
```

-continued

```
gtccaggctg gtgtcctctc tggtgatcag gatacaggtg atctggtact gcttgatgtt    1260
tgtcccctta cacttggtat tgaaactgtg ggaggagtca tgacaaaact gattccaagg    1320
aacactgtgg tacccaccaa gaagtctcag atcttctcca cggcttccga taatcagcca    1380
actgtaacaa tcaaggtcta tgaaggtgaa cgacccctaa caaaagacaa tcatcttctg    1440
ggtacatttg atctgactgg aattcctcct gctccccgtg gagttcccca gattgaagtc    1500
acttttgaga tagatgttaa tggtattatc cgagtgacag ctgaagacaa aggtacagga    1560
aacaaaaaca aaatcacaat taccaatgac caaaaccgcc tgacacctga gaaattgaa     1620 aggatggtta atgatgctga aagtttgct gaggaagaca aaaagctcaa agagcgcatt    1680
gacaccagga atgaattgga aagctatgct tattctctca agaaccagat tggagataaa    1740
gaaaagctgg gaggtaaact ttcttctgag ataaagaaa ccatggaaaa agctgtagag    1800
gaaaagattg aatggctgga aagccaccag gatgcggaca ttgaagactt taaagccaaa    1860
aagaaggaac tagaagaaat tgttcagcca attatcagca aactctatgg aagtggaggc    1920
cctcccccaa ctggtgaaga ggatacatca gaaaaagatg agttg                    1965
```

<210> SEQ ID NO 2
<211> LENGTH: 655
<212> TYPE: PRT
<213> ORGANISM: Mus musculus

<400> SEQUENCE: 2

```
Met Met Lys Phe Thr Val Val Ala Ala Leu Leu Leu Gly Ala
1               5                   10                  15

Val Arg Ala Glu Glu Asp Lys Lys Glu Asp Val Gly Thr Val Val
                20                  25                  30

Gly Ile Asp Leu Gly Thr Thr Tyr Ser Cys Val Gly Val Phe Lys Asn
            35                  40                  45

Gly Arg Val Glu Ile Ile Ala Asn Asp Gln Gly Asn Arg Ile Thr Pro
        50                  55                  60

Ser Tyr Val Ala Phe Thr Pro Glu Gly Glu Arg Leu Ile Gly Asp Ala
65                  70                  75                  80

Ala Lys Asn Gln Leu Thr Ser Asn Pro Glu Asn Thr Val Phe Asp Ala
                85                  90                  95

Lys Arg Leu Ile Gly Arg Thr Trp Asn Asp Pro Ser Val Gln Gln Asp
            100                 105                 110

Ile Lys Phe Leu Pro Phe Lys Val Val Glu Lys Thr Lys Pro Tyr
        115                 120                 125

Ile Gln Val Asp Ile Gly Gly Gly Gln Thr Lys Thr Phe Ala Pro Glu
    130                 135                 140

Glu Ile Ser Ala Met Val Leu Thr Lys Met Lys Glu Thr Ala Glu Ala
145                 150                 155                 160

Tyr Leu Gly Lys Lys Val Thr His Ala Val Val Thr Val Pro Ala Tyr
                165                 170                 175

Phe Asn Asp Ala Gln Arg Gln Ala Thr Lys Asp Ala Gly Thr Ile Ala
            180                 185                 190

Gly Leu Asn Val Met Arg Ile Ile Asn Glu Pro Thr Ala Ala Ala Ile
        195                 200                 205

Ala Tyr Gly Leu Asp Lys Arg Glu Gly Glu Lys Asn Ile Leu Val Phe
    210                 215                 220

Asp Leu Gly Gly Gly Thr Phe Asp Val Ser Leu Leu Thr Ile Asp Asn
225                 230                 235                 240
```

-continued

```
Gly Val Phe Glu Val Val Ala Thr Asn Gly Asp Thr His Leu Gly Gly
                245                 250                 255
Glu Asp Phe Asp Gln Arg Val Met Glu His Phe Ile Lys Leu Tyr Lys
            260                 265                 270
Lys Lys Thr Gly Lys Asp Val Arg Lys Asp Asn Arg Ala Val Gln Lys
        275                 280                 285
Leu Arg Arg Glu Val Glu Lys Ala Lys Arg Ala Leu Ser Ser Gln His
    290                 295                 300
Gln Ala Arg Ile Glu Ile Glu Ser Phe Phe Glu Gly Glu Asp Phe Ser
305                 310                 315                 320
Glu Thr Leu Thr Arg Ala Lys Phe Glu Glu Leu Asn Met Asp Leu Phe
                325                 330                 335
Arg Ser Thr Met Lys Pro Val Gln Glu Val Leu Glu Asp Ser Asp Leu
            340                 345                 350
Lys Lys Ser Asp Ile Asp Glu Ile Val Leu Val Gly Gly Ser Thr Arg
        355                 360                 365
Ile Pro Lys Ile Gln Gln Leu Val Lys Glu Phe Phe Asn Gly Lys Glu
    370                 375                 380
Pro Ser Arg Gly Ile Asn Pro Asp Glu Ala Val Ala Tyr Gly Ala Ala
385                 390                 395                 400
Val Gln Ala Gly Val Leu Ser Gly Asp Gln Asp Thr Gly Asp Leu Val
                405                 410                 415
Leu Leu Asp Val Cys Pro Leu Thr Leu Gly Ile Glu Thr Val Gly Gly
            420                 425                 430
Val Met Thr Lys Leu Ile Pro Arg Asn Thr Val Val Pro Thr Lys Lys
        435                 440                 445
Ser Gln Ile Phe Ser Thr Ala Ser Asp Asn Gln Pro Thr Val Thr Ile
    450                 455                 460
Lys Val Tyr Glu Gly Glu Arg Pro Leu Thr Lys Asp Asn His Leu Leu
465                 470                 475                 480
Gly Thr Phe Asp Leu Thr Gly Ile Pro Pro Ala Pro Arg Gly Val Pro
                485                 490                 495
Gln Ile Glu Val Thr Phe Glu Ile Asp Val Asn Gly Ile Ile Arg Val
            500                 505                 510
Thr Ala Glu Asp Lys Gly Thr Gly Asn Lys Asn Lys Ile Thr Ile Thr
        515                 520                 525
Asn Asp Gln Asn Arg Leu Thr Pro Glu Glu Ile Glu Arg Met Val Asn
    530                 535                 540
Asp Ala Glu Lys Phe Ala Glu Glu Asp Lys Lys Leu Lys Glu Arg Ile
545                 550                 555                 560
Asp Thr Arg Asn Glu Leu Glu Ser Tyr Ala Tyr Ser Leu Lys Asn Gln
                565                 570                 575
Ile Gly Asp Lys Glu Lys Leu Gly Gly Lys Leu Ser Ser Glu Asp Lys
            580                 585                 590
Glu Thr Met Glu Lys Ala Val Glu Glu Lys Ile Glu Trp Leu Glu Ser
        595                 600                 605
His Gln Asp Ala Asp Ile Glu Asp Phe Lys Ala Lys Lys Lys Glu Leu
    610                 615                 620
Glu Glu Ile Val Gln Pro Ile Ile Ser Lys Leu Tyr Gly Ser Gly Gly
625                 630                 635                 640
Pro Pro Pro Thr Gly Glu Glu Asp Thr Ser Glu Lys Asp Glu Leu
                645                 650                 655
```

<210> SEQ ID NO 3
<211> LENGTH: 1113
<212> TYPE: DNA
<213> ORGANISM: Mus musculus

<400> SEQUENCE: 3

| | | |
|---|---|---|
| atggtggtgg tggcagcggc gccgagcgcg gccacggcgg cccccaaagt gctactctta | 60 |
| tctggccagc ccgcctccgg cggccgggcg ctgccgctca tggtacccgg tccgcgggca | 120 |
| gcagggtcgg aggcgagcgg gacaccgcag gctcgcaagc ggcagcggct cacgcacctg | 180 |
| agcccggagg agaaagcgct gcggaggaaa ctgaaaaaca gagtagcagc gcagactgct | 240 |
| cgagatagaa agaaagcccg gatgagcgag ctggagcagc aagtggtgga tttggaagaa | 300 |
| gagaaccaca aactccagct agaaaatcag cttttacggg agaaaactca cggccttgtg | 360 |
| gttgagaacc aggagttaag aacacgcttg gaatggaca cgctggatcc tgacgaggtt | 420 |
| ccagaggtgg aggccaaggg gagtggagta aggctggtgg ccgggtctgc tgagtccgca | 480 |
| gcaggtgcag gcccagttgt cacctcccca gaacatcttc ccatggactc tgacactgtt | 540 |
| gcctcttcag attctgagtc tgatatcctt ttgggcattc tggacaagtt ggaccctgtc | 600 |
| atgttttca atgtccttc cccagagtct gctagtctgg aggaactccc agaggtctac | 660 |
| ccagaaggac ctagttcctt accagcctcc ctttctctgt cagtggggac ctcatcagcc | 720 |
| aagctggaag ccattaatga actcattcgt tttgaccatg tataccaa gcctctagtt | 780 |
| ttagagatcc cctctgagac agagagtcaa actaacgtgg tagtgaaaat tgaggaagca | 840 |
| cctctaagct cttcagaaga ggatcaccct gaattcattg tctcagtgaa gaaagagcct | 900 |
| ttggaagatg acttcatccc agagctgggc atctcaaacc tgctttcatc cagccattgt | 960 |
| ctgagaccac cttcttgcct gctggacgct cacagtgact gtggatatga gggctcccct | 1020 |
| tctcccttca gtgacatgtc ttctccactt ggtacagacc actcctggga ggatactttt | 1080 |
| gccaatgaac ttttccccca gctgattagt gtc | 1113 |

<210> SEQ ID NO 4
<211> LENGTH: 371
<212> TYPE: PRT
<213> ORGANISM: Mus musculus

<400> SEQUENCE: 4

Met Val Val Val Ala Ala Ala Pro Ser Ala Ala Thr Ala Ala Pro Lys
1               5                   10                  15

Val Leu Leu Leu Ser Gly Gln Pro Ala Ser Gly Gly Arg Ala Leu Pro
                20                  25                  30

Leu Met Val Pro Gly Pro Arg Ala Ala Gly Ser Glu Ala Ser Gly Thr
            35                  40                  45

Pro Gln Ala Arg Lys Arg Gln Arg Leu Thr His Leu Ser Pro Glu Glu
        50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn His Lys Leu Gln Leu Glu Asn Gln Leu Leu
            100                 105                 110

Arg Glu Lys Thr His Gly Leu Val Val Glu Asn Gln Glu Leu Arg Thr
        115                 120                 125

Arg Leu Gly Met Asp Thr Leu Asp Pro Asp Glu Val Pro Glu Val Glu
    130                 135                 140

```
Ala Lys Gly Ser Gly Val Arg Leu Val Ala Gly Ser Ala Glu Ser Ala
145                 150                 155                 160

Ala Gly Ala Gly Pro Val Val Thr Ser Pro Glu His Leu Pro Met Asp
            165                 170                 175

Ser Asp Thr Val Ala Ser Ser Asp Ser Glu Ser Asp Ile Leu Leu Gly
                180                 185                 190

Ile Leu Asp Lys Leu Asp Pro Val Met Phe Phe Lys Cys Pro Ser Pro
            195                 200                 205

Glu Ser Ala Ser Leu Glu Glu Leu Pro Glu Val Tyr Pro Glu Gly Pro
    210                 215                 220

Ser Ser Leu Pro Ala Ser Leu Ser Leu Ser Val Gly Thr Ser Ser Ala
225                 230                 235                 240

Lys Leu Glu Ala Ile Asn Glu Leu Ile Arg Phe Asp His Val Tyr Thr
                245                 250                 255

Lys Pro Leu Val Leu Glu Ile Pro Ser Glu Thr Glu Ser Gln Thr Asn
            260                 265                 270

Val Val Lys Ile Glu Glu Ala Pro Leu Ser Ser Ser Glu Glu Asp
    275                 280                 285

His Pro Glu Phe Ile Val Ser Val Lys Lys Glu Pro Leu Glu Asp Asp
    290                 295                 300

Phe Ile Pro Glu Leu Gly Ile Ser Asn Leu Leu Ser Ser Ser His Cys
305                 310                 315                 320

Leu Arg Pro Pro Ser Cys Leu Leu Asp Ala His Ser Asp Cys Gly Tyr
                325                 330                 335

Glu Gly Ser Pro Ser Pro Phe Ser Asp Met Ser Ser Pro Leu Gly Thr
            340                 345                 350

Asp His Ser Trp Glu Asp Thr Phe Ala Asn Glu Leu Phe Pro Gln Leu
    355                 360                 365

Ile Ser Val
    370

<210> SEQ ID NO 5
<211> LENGTH: 801
<212> TYPE: DNA
<213> ORGANISM: Mus musculus

<400> SEQUENCE: 5
atggtggtgg tggcagcggc gccgagcgcg gccacggcgg cccccaaagt gctactctta      60
tctggccagc ccgcctccgg cggccgggcg ctgccgctca tggtacccgg tccgcgggca     120
gcagggtcgg aggcgagcgg gacaccgcag gctcgcaagc ggcagcggct cacgcacctg     180
agcccggagg agaaagcgct gcggaggaaa ctgaaaaaca gtagcagc   cagactgct     240 cgagatagaa agaaagcccg gatgagcgag ctggagcagc aagtggtgga tttggaagaa     300
gagaaccaca aactccagct agaaaatcag cttttacggg agaaaactca cggccttgtg     360
gttgagaacc aggagttaag aacacgcttg gaatggaca cgctggatcc tgacgaggtt      420
ccagaggtgg aggccaaggg gagtggagta aggctggtgg ccgggtctgc tgagtccgca     480
gcactcagac tatgtgcacc tctgcagcag gtgcaggccc agttgtcacc tccccagaac     540
atcttcccat ggactctgac actgttgcct cttcagattc tgagtctgat atccttttgg     600
gcattctgga caagttggac cctgtcatgt ttttcaaatg tccttcccca gagtctgcta     660
gtctggagga actcccagag gtctacccag aaggacctag ttccttacca gcctcccttt     720
ctctgtcagt ggggacctca tcagccaagc tggaagccat taatgaactc attcgttttg     780
```
accatgtata caccaagcct c    801

<210> SEQ ID NO 6
<211> LENGTH: 267
<212> TYPE: PRT
<213> ORGANISM: Mus musculus

<400> SEQUENCE: 6

Met Val Val Val Ala Ala Ala Pro Ser Ala Thr Ala Ala Pro Lys
1               5                   10                  15

Val Leu Leu Leu Ser Gly Gln Pro Ala Ser Gly Gly Arg Ala Leu Pro
            20                  25                  30

Leu Met Val Pro Gly Pro Arg Ala Ala Gly Ser Glu Ala Ser Gly Thr
                35                  40                  45

Pro Gln Ala Arg Lys Arg Gln Arg Leu Thr His Leu Ser Pro Glu Glu
            50                  55                  60

Lys Ala Leu Arg Arg Lys Leu Lys Asn Arg Val Ala Ala Gln Thr Ala
65                  70                  75                  80

Arg Asp Arg Lys Lys Ala Arg Met Ser Glu Leu Glu Gln Gln Val Val
                85                  90                  95

Asp Leu Glu Glu Glu Asn His Lys Leu Gln Leu Glu Asn Gln Leu Leu
            100                 105                 110

Arg Glu Lys Thr His Gly Leu Val Val Glu Asn Gln Glu Leu Arg Thr
            115                 120                 125

Arg Leu Gly Met Asp Thr Leu Asp Pro Asp Glu Val Pro Glu Val Glu
            130                 135                 140

Ala Lys Gly Ser Gly Val Arg Leu Val Ala Gly Ser Ala Glu Ser Ala
145                 150                 155                 160

Ala Leu Arg Leu Cys Ala Pro Leu Gln Gln Val Gln Ala Gln Leu Ser
                165                 170                 175

Pro Pro Gln Asn Ile Phe Pro Trp Thr Leu Thr Leu Leu Pro Leu Gln
            180                 185                 190

Ile Leu Ser Leu Ile Ser Phe Trp Ala Phe Trp Thr Ser Trp Thr Leu
            195                 200                 205

Ser Cys Phe Ser Asn Val Leu Pro Gln Ser Leu Leu Val Trp Arg Asn
210                 215                 220

Ser Gln Arg Ser Thr Gln Lys Asp Leu Val Pro Tyr Gln Pro Pro Phe
225                 230                 235                 240

Leu Cys Gln Trp Gly Pro His Gln Pro Ser Trp Lys Pro Leu Met Asn
                245                 250                 255

Ser Phe Val Leu Thr Met Tyr Thr Pro Ser Leu
            260                 265

<210> SEQ ID NO 7
<211> LENGTH: 504
<212> TYPE: DNA
<213> ORGANISM: Mus musculus

<400> SEQUENCE: 7
atggcagctg agtccctgcc tttcaccttg gagacggtgt ccagctggga gctggaagcc    60
tggtatgagg atctgcagga ggtcctgtcc tcagatgaaa tgggggcac ctatatctca    120 tccccaggaa acgaagagga agaatcaaaa accttcacta ctcttgaccc tgcgtcccta    180
gcttggctga cagaggagcc agggccaaca gaggtcacac gcacatccca aagccctcgc    240
tctccagatt ccagtcagag ttctatggcc caggaggaag aggaggaaga gcaaggaaga    300

```
actaggaaac ggaaacagag tggtcagtgc ccagcccggc ctgggaagca acgcatgaag    360
gagaaggagc aggagaacga gcggaaagtg gcacagctag ctgaagagaa cgagcggctc    420
aagcaggaaa tcgagcgcct gaccagggag gtggagacca cacggcgggc tctgatcgac    480
cgcatggtca gcctgcacca agca                                           504
```

```
<210> SEQ ID NO 8
<211> LENGTH: 168
<212> TYPE: PRT
<213> ORGANISM: Mus musculus

<400> SEQUENCE: 8
```

```
Met Ala Ala Glu Ser Leu Pro Phe Thr Leu Glu Thr Val Ser Ser Trp
 1               5                  10                  15

Glu Leu Glu Ala Trp Tyr Glu Asp Leu Gln Glu Val Leu Ser Ser Asp
            20                  25                  30

Glu Asn Gly Gly Thr Tyr Ile Ser Ser Pro Gly Asn Glu Glu Glu Glu
        35                  40                  45

Ser Lys Thr Phe Thr Thr Leu Asp Pro Ala Ser Leu Ala Trp Leu Thr
    50                  55                  60

Glu Glu Pro Gly Pro Thr Glu Val Thr Arg Thr Ser Gln Ser Pro Arg
65                  70                  75                  80

Ser Pro Asp Ser Ser Gln Ser Ser Met Ala Gln Glu Glu Glu Glu Glu
                85                  90                  95

Glu Gln Gly Arg Thr Arg Lys Arg Lys Gln Ser Gly Gln Cys Pro Ala
            100                 105                 110

Arg Pro Gly Lys Gln Arg Met Lys Glu Lys Glu Gln Glu Asn Glu Arg
        115                 120                 125

Lys Val Ala Gln Leu Ala Glu Glu Asn Glu Arg Leu Lys Gln Glu Ile
    130                 135                 140

Glu Arg Leu Thr Arg Glu Val Glu Thr Thr Arg Arg Ala Leu Ile Asp
145                 150                 155                 160

Arg Met Val Ser Leu His Gln Ala
                165
```

```
<210> SEQ ID NO 9
<211> LENGTH: 1962
<212> TYPE: DNA
<213> ORGANISM: Homo sapiens

<400> SEQUENCE: 9
```

```
atgaagctct ccctggtggc cgcgatgctg ctgctgctca gcgcggcgcg ggccgaggag     60
gaggacaaga aggaggacgt gggcacggtg gtcggcatcg acctgggggac cacctactcc   120 tgcgtcggcg tgttcaagaa cggccgcgtg gagatcatcg ccaacgatca gggcaaccgc   180
atcacgccgt cctatgtcgc cttcactcct gaaggggaac gtctgattgg cgatgccgcc   240
aagaaccagc tcacctccaa ccccgagaac acggtctttg acgccaagcg gctcatcggc   300
cgcacgtgga tgaccccgtc tgtgcagcag gacatcaagt tcttgccgtt caaggtggtt   360
gaaaagaaaa ctaaaccata cattcaagtt gatattggag gtgggcaaac aaagacattt   420
gctcctgaag aaatttctgc catggttctc actaaaatga agaaaccgc tgaggcttat   480 ttgggaaaga aggttaccca tgcagttgtt actgtaccag cctatttaa tgatgcccaa   540 cgccaagcaa ccaaagacgc tggaactatt gctggcctaa atgttatgag gatcatcaac   600
gagcctacgg cagctgctat tgcttatggc ctggataaga gggagggga gaagaacatc   660
```

```
ctggtgtttg aacctgggtgg cggaaccttc gatgtgtctc ttctcaccat tgacaatggt      720
gtcttcgaag ttgtggccac taatggagat actcatctgg gtggagaaga ctttgaccag      780
cgtgtcatgg aacacttcat caaactgtac aaaaagaaga cgggcaaaga tgtcaggaaa      840
gacaatagag ctgtgcagaa actccggcgc gaggtagaaa aggccaaacg ggccctgtct      900
tctcagcatc aagcaagaat tgaaattgag tccttctatg aaggagaaga cttttctgag      960
accctgactc gggccaaatt tgaagagctc aacatggatc tgttccggtc tactatgaag     1020
cccgtccaga agtgttgga agattctgat ttgaagaagt ctgatattga tgaaattgtt      1080
cttgttggtg gctcgactcg aattccaaag attcagcaac tggttaaaga gttcttcaat     1140
ggcaaggaac catcccgtgg cataaaccca gatgaagctg tagcgtatgg tgctgctgtc     1200
caggctggtg tgctctctgg tgatcaagat acaggtgacc tggtactgct tgatgtatgt     1260
ccccttacac ttggtattga aactgtggga ggtgtcatga ccaaactgat tccaaggaac     1320
acagtggtgc ctaccaagaa gtctcagatc ttttctacag cttctgataa tcaaccaact     1380
gttacaatca aggtctatga aggtgaaaga ccctgacaa agacaatca tcttctgggt       1440 acatttgatc tgactggaat tcctcctgct cctcgtgggg tcccacagat tgaagtcacc     1500
tttgagatag atgtgaatgg tattcttcga gtgacagctg aagacaaggg tacagggaac     1560
aaaaataaga tcacaatcac caatgaccag aatcgcctga cacctgaaga aatcgaaagg     1620
atggttaatg atgctgagaa gtttgctgag gaagacaaaa agctcaagga gcgcattgat     1680
actagaaatg agttggaaag ctatgcctat tctctaaaga atcagattgg agataaagaa     1740
aagctgggag gtaaactttc ctctgaagat aaggagacca tggaaaaagc tgtagaagaa     1800
aagattgaat ggctggaaag ccaccaagat gctgacattg aagacttcaa agctaagaag     1860
aaggaactgg aagaaattgt tcaaccaatt atcagcaaac tctatggaag tgcaggccct     1920
cccccaactg gtgaagagga tacagcagaa aaagatgagt tg                        1962
```

<210> SEQ ID NO 10
<211> LENGTH: 654
<212> TYPE: PRT
<213> ORGANISM: Homo sapiens

<400> SEQUENCE: 10

```
Met Lys Leu Ser Leu Val Ala Ala Met Leu Leu Leu Ser Ala Ala
1               5                   10                  15

Arg Ala Glu Glu Glu Asp Lys Lys Glu Asp Val Gly Thr Val Gly
                20                  25                  30

Ile Asp Leu Gly Thr Thr Tyr Ser Cys Val Gly Val Phe Lys Asn Gly
            35                  40                  45

Arg Val Glu Ile Ile Ala Asn Asp Gln Gly Asn Arg Ile Thr Pro Ser
        50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
    130                 135                 140
```

```
Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
370                 375                 380

Ser Arg Gly Ile Asn Pro Asp Glu Ala Val Ala Tyr Gly Ala Ala Val
385                 390                 395                 400

Gln Ala Gly Val Leu Ser Gly Asp Gln Asp Thr Gly Asp Leu Val Leu
                405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Val Pro Thr Lys Lys Ser
        435                 440                 445

Gln Ile Phe Ser Thr Ala Ser Asp Asn Gln Pro Thr Val Thr Ile Lys
450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
                485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
        515                 520                 525

Asp Gln Asn Arg Leu Thr Pro Glu Glu Ile Glu Arg Met Val Asn Asp
530                 535                 540

Ala Glu Lys Phe Ala Glu Glu Asp Lys Lys Leu Lys Glu Arg Ile Asp
545                 550                 555                 560
```

```
Thr Arg Asn Glu Leu Glu Ser Tyr Ala Tyr Ser Leu Lys Asn Gln Ile
                565                 570                 575
Gly Asp Lys Glu Lys Leu Gly Gly Lys Leu Ser Ser Glu Asp Lys Glu
            580                 585                 590
Thr Met Glu Lys Ala Val Glu Glu Lys Ile Glu Trp Leu Glu Ser His
        595                 600                 605
Gln Asp Ala Asp Ile Glu Asp Phe Lys Ala Lys Lys Glu Leu Glu
    610                 615                 620
Glu Ile Val Gln Pro Ile Ile Ser Lys Leu Tyr Gly Ser Ala Gly Pro
625                 630                 635                 640
Pro Pro Thr Gly Glu Glu Asp Thr Ala Glu Lys Asp Glu Leu
                645                 650

<210> SEQ ID NO 11
<211> LENGTH: 783
<212> TYPE: DNA
<213> ORGANISM: Homo sapiens

<400> SEQUENCE: 11
atggtggtgg tggcagccgc gccgaacccg gccgacggga cccctaaagt tctgcttctg      60
tcggggcagc ccgcctccgc cgccggagcc ccggccggcc aggccctgcc gctcatggtg     120
ccagcccaga gagggccag cccggaggca gcgagcgggg ggctgcccca ggcgcgcaag      180
cgacagcgcc tcacgcacct gagccccgag gagaaggcgc tgaggaggaa actgaaaaac     240
agagtagcag ctcagactgc cagagatcga agaaggctc gaatgagtga gctggaacag     300
caagtggtag atttagaaga agagaaccaa aaacttttgc tagaaaatca gcttttacga     360
gagaaaactc atggccttgt agttgagaac caggagttaa gacagcgctt ggggatggat     420
gccctggttg ctgaagagga ggcggaagcc aagggggaatg aagtgaggcc agtggccggg     480
tctgctgagt ccgcagcact cagactacgt gcacctctgc agcaggtgca ggcccagttg     540 tcaccctcc agaacatctc cccatggatt ctggcggtat tgactcttca gattcagagt     600
ctgatatcct gttgggcatt ctggacaact tggacccagt catgttcttc aaatgccctt     660
ccccagagcc tgccagcctg gaggagctcc cagaggtcta cccagaagga cccagttcct     720
taccagcctc cctttctctg tcagtgggga cgtcatcagc caagctggaa gccattaatg     780
aac                                                                   783

<210> SEQ ID NO 12
<211> LENGTH: 261
<212> TYPE: PRT
<213> ORGANISM: Homo sapiens

<400> SEQUENCE: 12

Met Val Val Val Ala Ala Ala Pro Asn Pro Ala Asp Gly Thr Pro Lys
1               5                   10                  15
Val Leu Leu Leu Ser Gly Gln Pro Ala Ser Ala Ala Gly Ala Pro Ala
                20                  25                  30
Gly Gln Ala Leu Pro Leu Met Val Pro Ala Gln Arg Gly Ala Ser Pro
            35                  40                  45
Glu Ala Ala Ser Gly Gly Leu Pro Gln Ala Arg Lys Arg Gln Arg Leu
        50                  55                  60
Thr His Leu Ser Pro Glu Glu Lys Ala Leu Arg Arg Lys Leu Lys Asn
65                  70                  75                  80
Arg Val Ala Ala Gln Thr Ala Arg Asp Arg Lys Lys Ala Arg Met Ser
                85                  90                  95
```

-continued

Glu Leu Glu Gln Gln Val Val Asp Leu Glu Glu Glu Asn Gln Lys Leu
            100                 105                 110

Leu Leu Glu Asn Gln Leu Leu Arg Glu Lys Thr His Gly Leu Val Val
        115                 120                 125

Glu Asn Gln Glu Leu Arg Gln Arg Leu Gly Met Asp Ala Leu Val Ala
        130                 135                 140

Glu Glu Glu Ala Glu Ala Lys Gly Asn Glu Val Arg Pro Val Ala Gly
145                 150                 155                 160

Ser Ala Glu Ser Ala Ala Leu Arg Leu Arg Ala Pro Leu Gln Gln Val
                165                 170                 175

Gln Ala Gln Leu Ser Pro Leu Gln Asn Ile Ser Pro Trp Ile Leu Ala
            180                 185                 190

Val Leu Thr Leu Gln Ile Gln Ser Leu Ile Ser Cys Trp Ala Phe Trp
        195                 200                 205

Thr Thr Trp Thr Gln Ser Cys Ser Ser Asn Ala Leu Pro Gln Ser Leu
        210                 215                 220

Pro Ala Trp Arg Ser Ser Gln Arg Ser Thr Gln Lys Asp Pro Val Pro
225                 230                 235                 240

Tyr Gln Pro Pro Phe Leu Cys Gln Trp Gly Arg His Gln Pro Ser Trp
                245                 250                 255

Lys Pro Leu Met Asn
            260

<210> SEQ ID NO 13
<211> LENGTH: 1386
<212> TYPE: DNA
<213> ORGANISM: Homo sapiens

<400> SEQUENCE: 13
atggcctcaa acgattatac ccaacaagca acccaaagct atggggccta ccccacccag      60
cccgggcagg gctattccca gcagagcagt cagccctacg acagcagag ttacagtggt     120
tatagccagt ccacggacac ttcaggctat ggccagagca gctattcttc ttatggccag     180
agccagaaca caggctatgg aactcagtca actccccagg atatggctc gactggcggc     240
tatggcagta gccagagctc ccaatcgtct tacgggcagc agtcctccta ccctggctat     300
ggccagcagc agctcccag cagcacctcg ggaagttacg gtagcagttc tcagagcagc     360
agctatgggc agccccagag tgggagctac agccagcagc ctagctatgg tggacagcag     420
caaagctatg gacagcagca aagctataat ccccctcagg gctatggaca gcagaaccag     480
tacaacagca gcagtggtgg tggaggtgga ggtggaggtg gaggtaacta tggccaagat     540
caatcctcca tgagtagtgg tggtggcagt ggtggcggtt atggcaatca agaccagagt     600
ggtggaggtg gcagcggtgg ctatggacag caggaccgtg gaggccgcgg caggggtggc     660
agtggtggcg gcggcggcgg cggcggtggt ggttacaacc gcagcagtgg tggctatgaa     720
cccagaggtc gtggaggtgg ccgtggaggc agaggtggca tgggcggaag tgaccgtggt     780
ggcttcaata aatttggtgt gttcaagaag gaagtgtatc ttcatacatc accacacctg     840
aaagcagatg tgcttttcca gactgatcca actgcagaga tggcagctga gtcattgcct     900
ttctcctccg gagacactgt gcagctggag ctggaagcct ggtatgagga cctgcaagag     960
gtcctgtctt cagatgaaaa tgggggtacc tatgtttcac ctcctggaaa tgaaggaaa    1020
gaatcaaaaa tcttcaccac tcttgaccct gcttctctgg cttggctgac tgaggaggag    1080
ccagaaccag cagaggtcac aagcacctcc agagccctc actctccaga ttccagtcag    1140

-continued

```
agctccctgg ctcaggagga agaggaggaa gaccaaggga gaaccaggaa acggaaacag    1200
agtggtcatt ccccagcccg ggctggaaag cagcgcatga aggagaaaga acaggagaat    1260
gaaaggaaag tggcacagct agctgaagag aatgaacggc tcaagcagga aatcgagcgc    1320
ctgaccaggg aagtagaggc gactcgccga gctctgattg accgaatggt gaatctgcac    1380
caagca                                                               1386
```

<210> SEQ ID NO 14
<211> LENGTH: 462
<212> TYPE: PRT
<213> ORGANISM: Homo sapiens

<400> SEQUENCE: 14

```
Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Ser Tyr Gly Gln Pro Gln Ser Gly
        115                 120                 125

Ser Tyr Ser Gln Gln Pro Ser Tyr Gly Gly Gln Gln Ser Tyr Gly
    130                 135                 140

Gln Gln Gln Ser Tyr Asn Pro Pro Gln Gly Tyr Gly Gln Gln Asn Gln
145                 150                 155                 160

Tyr Asn Ser Ser Gly Gly Gly Gly Gly Gly Gly Gly Gly Gly Asn
                165                 170                 175

Tyr Gly Gln Asp Gln Ser Ser Met Ser Ser Gly Gly Gly Ser Gly Gly
            180                 185                 190

Gly Tyr Gly Asn Gln Asp Gln Ser Gly Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Gly Tyr Asn Arg Ser Ser Gly Gly Tyr Glu
225                 230                 235                 240

Pro Arg Gly Arg Gly Gly Arg Gly Gly Arg Gly Gly Met Gly Gly
                245                 250                 255

Ser Asp Arg Gly Gly Phe Asn Lys Phe Gly Val Phe Lys Lys Glu Val
            260                 265                 270

Tyr Leu His Thr Ser Pro His Leu Lys Ala Asp Val Leu Phe Gln Thr
        275                 280                 285

Asp Pro Thr Ala Glu Met Ala Ala Glu Ser Leu Pro Phe Ser Phe Gly
    290                 295                 300

Thr Leu Ser Ser Trp Glu Leu Glu Ala Trp Tyr Glu Asp Leu Gln Glu
305                 310                 315                 320
```

```
Val Leu Ser Ser Asp Glu Asn Gly Gly Thr Tyr Val Ser Pro Pro Gly
            325                 330                 335

Asn Glu Glu Glu Ser Lys Ile Phe Thr Thr Leu Asp Pro Ala Ser
            340                 345                 350

Leu Ala Trp Leu Thr Glu Glu Pro Glu Pro Ala Glu Val Thr Ser
            355                 360                 365

Thr Ser Gln Ser Pro His Ser Pro Asp Ser Ser Gln Ser Ser Leu Ala
        370                 375                 380

Gln Glu Glu Glu Glu Asp Gln Gly Arg Thr Arg Lys Arg Lys Gln
385                 390                 395                 400

Ser Gly His Ser Pro Ala Arg Ala Gly Lys Gln Arg Met Lys Glu Lys
                405                 410                 415

Glu Gln Glu Asn Glu Arg Lys Val Ala Gln Leu Ala Glu Glu Asn Glu
            420                 425                 430

Arg Leu Lys Gln Glu Ile Glu Arg Leu Thr Arg Glu Val Glu Ala Thr
        435                 440                 445

Arg Arg Ala Leu Ile Asp Arg Met Val Asn Leu His Gln Ala
        450                 455                 460

<210> SEQ ID NO 15
<211> LENGTH: 49
<212> TYPE: DNA
<213> ORGANISM: Artificial
<220> FEATURE:
<223> OTHER INFORMATION: Nucleic acid sequence encoding a short
      interfering RNA of the short hairpin type which targets CHOP
      transcripts.

<400> SEQUENCE: 15
acgaagagga agaatcaaat tcaagagatt tgattcttcc tcttcgttt          49

<210> SEQ ID NO 16
<211> LENGTH: 49
<212> TYPE: DNA
<213> ORGANISM: Artificial
<220> FEATURE:
<223> OTHER INFORMATION: Nucleic acid sequence encoding a short
      interfering RNA of the short hairpin type which targets CHOP
      transcripts.

<400> SEQUENCE: 16
gaactaggaa acggaaacat tcaagagatg tttccgtttc ctagttctt          49
```

METHODS FOR ALTERING PROTEIN PRODUCTION RATES

CROSS-REFERENCE TO RELATED APPLICATION

This application claims the benefit of U.S. Provisional Application No. 60/558,239, filed Mar. 31, 2004.

FIELD OF THE INVENTION

This invention relates to methods for altering the cellular secretion rate of a protein.

BACKGROUND OF THE INVENTION

Large-scale production of proteins, such as antibodies, typically relies on secretion of the protein from a cultured production cell line. Secreted proteins produced by cultured cells can be readily recovered and purified from the surrounding cell culture media.

The cellular secretion rate of proteins is an important parameter affecting the production and purification of secreted proteins from a bioreactor or other system. In general, higher purified protein yields can be attained when the cellular secretion rate is relatively high. Conversely, if the cellular secretion rate is too low protein purification may not be feasible.

One approach to circumventing the problem of low secreting cells has been to isolate high secreting, subcloned cells from a population of low secreting cells. Typically, this requires several time and labor-intensive rounds of limiting serial dilution, screening and selection of high secreting cell lines. Alternatively, entirely new cell lines producing the protein of interest are generated in the hope that the new cell lines will be high secreting lines.

Each of the foregoing approaches to generating high secreting cell lines has limitations. For example, identifying high secreting cell lines by subcloning from a population of low secreting cells is limited by the relative rarity of high secreting cells in the population as well as the extensive amounts of time and labor required for the identification of any high secreting cells.

Further, the generation of new cell lines producing the antibody or protein of interest is limited by the possibility that the new cell lines will not be high secreting and the substantial amounts of effort required to re-generate antibody producing cells and identify high secreting cells. In some instances, only low secreting cell lines can be obtained due to protein misfolding inside the endoplasmic reticulum (ER) of the cell resulting in a decreased secretion rate.

Thus, a need exists for effective methods of changing the cellular secretion rate of a protein.

SUMMARY OF THE INVENTION

Figure 1:
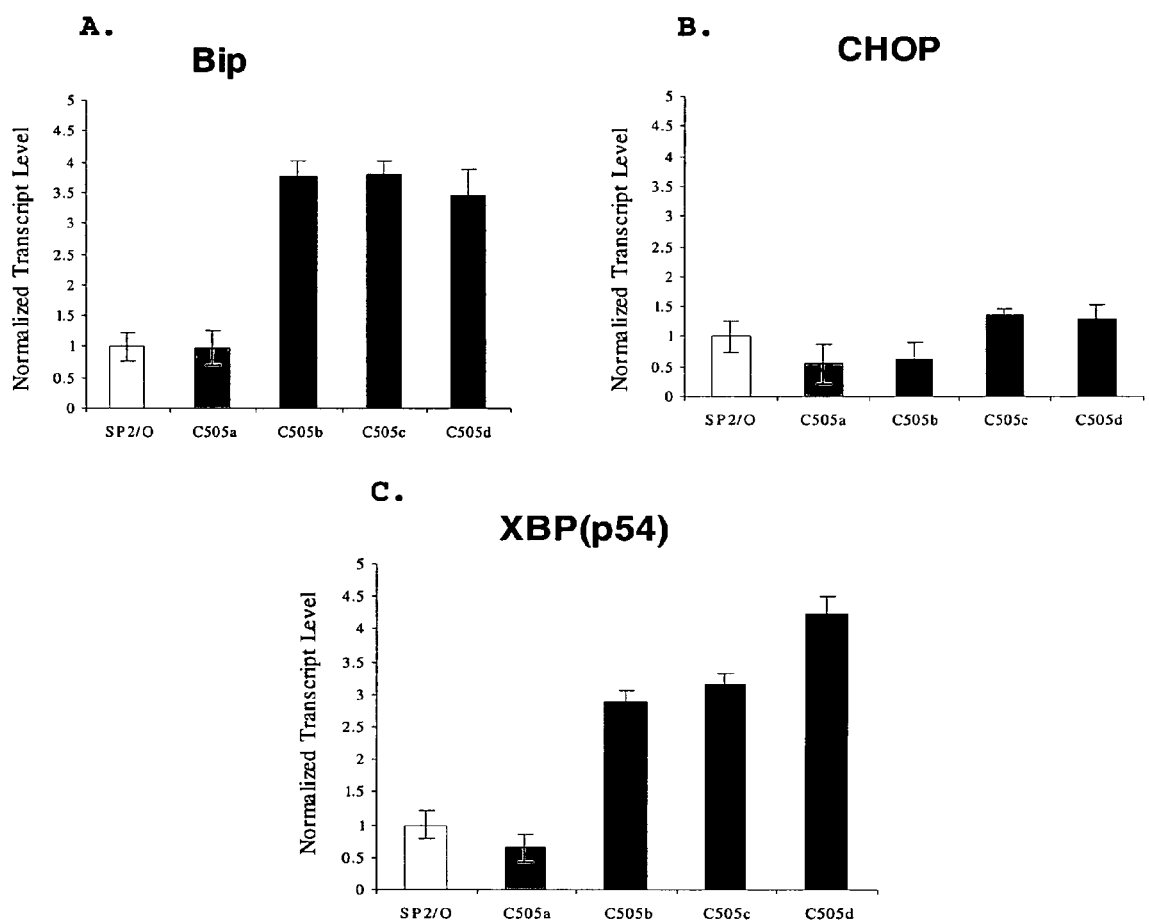
FIG. 1 shows UPR gene transcript levels in cells secreting mAbs at high rates.

One aspect of the invention is a method for altering the cellular secretion rate of a protein comprising the steps of modulating the activity of at least one UPR pathway component in a cell; and culturing the cells.

Another aspect of the invention is a plasma cell with a changed cellular secretion rate generated by altering the cellular secretion rate of a protein comprising the steps of modulating the activity of at least one unfolded protein response (UPR) pathway component in a cell; and culturing the cells.

Another aspect of the invention is a transgenic animal comprising a plasma cell with a changed cellular secretion rate generated by modulating the activity of at least one UPR pathway component in a cell and culturing the cells.

Another aspect of the invention is an isolated nucleic acid having the sequence shown in SEQ ID NO: 15 or SEQ ID NO: 16.

DETAILED DESCRIPTION OF THE INVENTION

All publications, including but not limited to patents and patent applications, cited in this specification are herein incorporated by reference as though fully set forth.

The term "antibodies" as used herein is meant in a broad sense and includes immunoglobulin or antibody molecules including polyclonal antibodies, monoclonal antibodies including murine, human, humanized and chimeric monoclonal antibodies and antibody fragments or variants. Antibodies are secreted proteins constitutively expressed and secreted by plasma cells. Antibodies can also be produced using plasma cells immortalized by standard methods such as hybridoma generation or by transfection of antibody heavy and/or light chain genes into an immortalized B cell such as a myeloma cell or other cell types such as Chinese hamster ovary (CHO) cells, plant cells and insect cells.

Antibody fragments or variants include mimetibodies, Fab fragments, F(ab')$_2$ fragments, Fc fragments, heavy chain fragments, light chain fragments, and molecules containing a portion of at least one antibody peptide chain. Such portions may correspond to antibody variable, hinge, or constant region peptide chains.

The term "mimetibody" as used herein means a protein having the generic formula (I):

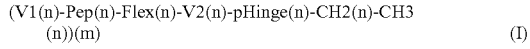

$$(V1(n)\text{-}Pep(n)\text{-}Flex(n)\text{-}V2(n)\text{-}pHinge(n)\text{-}CH2(n)\text{-}CH3(n))(m) \quad (I)$$

where V1 is at least one portion of an N-terminus of an immunoglobulin variable region, Pep is at least one bioactive peptide that binds to an epitope, Flex is polypeptide that provides structural flexibility by allowing the mimetibody to have alternative orientations and binding properties, V2 is at least one portion of a C-terminus of an immunoglobulin variable region, pHinge is at least a portion of an immunoglobulin hinge region, CH2 is at least a portion of an immunoglobulin CH2 constant region and CH3 is at least a portion of an immunoglobulin CH3 constant region, where n and m can be an integer between 1 and 10. A mimetibody can mimic properties and functions of different types of immunoglobulin molecules such as IgG1, IgG2, IgG3, IgG4, IgA, IgM, IgD and IgE dependent on the heavy chain constant domain amino acid sequence present in the construct.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., *Nature* 256: 495 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., *Proc. Natl Acad Sci (USA)*, 86: 10029-10032, (1989) and Hodgson et al., *Bio/Technology*, 9: 421, (1991).

Fully human mAbs lacking any non-human sequences can be prepared from human immunoglobulin transgenic mice by techniques referenced in, e.g., Lonberg et al., *Nature* 368: 856-859, (1994); Fishwild et al., *Nature Biotechnology* 14: 845-851, (1996), and Mendez et al., *Nature Genetics* 15: 146-156, (1997). Human mAbs can also be prepared and optimized from phage display libraries by techniques referenced in, e.g., Knappik et al., *J. Mol. Biol.* 296: 57-86, (2000) and Krebs et al., *J. Immunol. Meth.* 254: 67-84, (2001).

The term "cellular secretion rate" as used herein means the rate at which a cell secretes a given protein. Such rates may be described as the change in the amount of protein present in the culture media per change in time or can be normalized to cell number and expressed with units "pg/cell/day."

The term "short interfering RNA" as used herein means a nucleic acid sequence that mediates the cleavage of a target gene transcript. Short interfering RNAs (siRNAs) may be double stranded or of the short hairpin type. Double stranded siRNAs may be comprised of two individual, antiparallel, annealed RNA strands or annealed nucleic acid strands which contain both RNA and DNA (e.g. 5'-TTTTUUUU-3' annealed to 5'-TTTTUUUU-3' or 5'-TTTT-3' annealed to 5'-UUUU-3'). siRNAs of the short hairpin type may be comprised of a single RNA strand or a single RNA:DNA hybrid strand capable of forming a stem-and-loop structure or other secondary structure effective as an siRNA. Those skilled in the art will recognize that siRNAs may comprise other modifications such as nucleoside analogs, backbone modifications, and other modifications that still permit the modified siRNA nucleic acid to mediate the cleavage of a target gene transcript.

The term "small molecule" as used herein means a compound with a molecular weight less than 24,000 g/mol which is not comprised solely of amino acid residues or nucleic acid residues.

The term "transcriptional control sequence" as used herein means a nucleic acid sequence which is necessary for the transcription of a gene or a nucleic acid sequence which increases or decreases the transcription of a gene.

The term "UPR pathway component" as used herein and in the claims means peptide chains or nucleic acid sequences, such as transcriptional control sequences, which mediate signaling through the UPR pathway or activate the UPR.

The present invention provides methods useful for altering the cellular secretion rate of a protein by a cell. An exemplary use of the methods of the invention is enhancement of secretion rates for proteins that are useful for therapeutic, diagnostic or research purposes, such as antibodies.

Low protein secretion rates in cell lines can be caused by the accumulation of misfolded proteins in the cell ER slowing or stopping the secretion process via the UPR. Stress-sensing proteins in the ER membrane detect an excess of unfolded protein and trigger the UPR. Subsequently, via a complex signal transduction cascade, a chaperone protein Bip and transcription factors XBP-1 and CHOP are upregulated.

Chaperone proteins bind to unfolded proteins and assist in correct folding. The transcription factor CHOP is generally considered as a negative regulator of cell growth, differentiation and survival. It has been observed that upregulation of CHOP causes cell cycle arrest, thus giving the cell time to cope with the unfavorable conditions responsible for UPR induction.

The transcription factor XBP-1 is required for generating plasma cells, the differentiated B lymphocytes that secrete large amounts of immunoglobulins. Plasma cells display an altered UPR in which an upregulation of some UPR genes occurs prior to immunoglobulin synthesis. These include XBP-1, Bip, Grp94 and p50ATF6 alpha and their upregulation are necessary for plasma cell differentiation and proper antibody secretion. (Gass, J. N., et al., *J. Biol. Chem.* 227, 49047-49054 (2002). In contrast, CHOP is not upregulated during this transition, suggesting a distinct type of UPR. The upregulation of these molecules can have a beneficial or detrimental effect causing either increases in the cellular protein secretion rate or apoptosis. See Kaufman, R. J., *Genes Dev.* 13, 1211-1233 (1999) and Cudna, R. E., et al., *Biotechnol. Bioeng.* 81, 56-65 (2003).

In a method of the invention, the cellular secretion rate of a protein is altered by modulating the activity of at least one UPR pathway component in a cell and culturing the cell. The method of the invention provides for increasing or decreasing the cellular secretion rate of a protein such as an antibody.

In an embodiment of the invention, the cellular secretion rate of a protein is increased by stably transfecting the cell with a nucleic acid encoding a UPR pathway component. UPR pathway components may be polypeptides or nucleic acid sequences, such as a transcriptional control sequence, which mediate signaling through the UPR pathway or activate the UPR. Examples of UPR pathway components include BiP, XBP and CHOP and variants having similar activity. Other examples of UPR pathway components include IRE1, PERK, ATF4, ATF6, eIF2alpha, GRP78, GRP94, calreticulin, chaperones, and variants having similar activity (see e.g. Cudna and Dickson, *Biotechnol. Bioeng.*, 81, 56-65 (2002)). An example of a transcriptional control sequence is the cis-acting UPR element (UPRE) and ERSE which have been identified in the promoters of different UPR genes. Those of ordinary skill in the art will recognize other UPR pathway components and transcriptional control sequences. The UPR pathway component can have an amino acid sequence as shown in SEQ ID NO: 2 (murine BiP), SEQ ID NO: 4 (murine XBP-1, spliced form), SEQ ID NO: 6 (murine XBP-1, unspliced form), SEQ ID NO: 8 (murine CHOP-10), SEQ ID NO: 10 (human BiP), SEQ ID NO: 12 (human XBP-1) or SEQ ID NO: 14 (human CHOP-10). The UPR pathway component nucleic acid can have a sequence as shown in SEQ ID NO: 1 (murine BiP mRNA), SEQ ID NO: 3 (murine XBP-1, spliced form mRNA), SEQ ID NO: 5

(murine XBP-1, unspliced form, mRNA), SEQ ID NO: 7 (murine CHOP-10 mRNA), SEQ ID NO: 9 (human BiP mRNA), SEQ ID NO: 11 (human XBP-1 mRNA), SEQ ID NO: 13 (human CHOP-10 mRNA).

Variants of these sequences having an activity similar to the parent molecule will also be useful in the methods of the invention. For example, variant molecules having at least 80% identity to the parent molecule would be expected to have similar activity. Percent identity between two protein sequences can be determined using the BLASTP algorithm with filtering turned off and all other default settings unchanged. Different isoforms of a polypeptide, dominant negative versions of a polypeptide, or covalently modified forms of a polypeptide are some examples of variants of a parent molecule.

In another embodiment of the invention, the cellular secretion rate of a protein can be decreased by decreasing the expression of a UPR pathway component. Gene expression of a UPR pathway component such as BiP or CHOP can be decreased by of a cell with short interfering RNA (siRNA) molecules or antisense molecules.

In another embodiment of the invention, the cellular secretion rate of a protein is increased by modulating the UPR pathway component through administration of a small molecule. An exemplary small molecule is thapsigargin, a UPR induction agent (Litton, J., *J. Biol. Chem.* 26, 17067-17071 (1991). Other examples of such small molecules include tunicamycin and lipopolysaccharide.

In another embodiment of the invention, the cellular secretion rate of a protein is increased by placing the cells in static growth phase. Cells may be placed in static growth phase by limiting nutrient availability, allowing cellular wastes to accumulate or changing the pH of the cell culture media. Those skilled in the art will also recognize other methods for placing cells in the static growth phase.

In the methods of the invention, exemplary cells are plasma cells, i.e., differentiated B-cells that secrete antibodies. Plasma cells may be isolated from murine, human, or other animal sources. Typically, the plasma cells have been immortalized by standard techniques such as viral infection, with Epstein-Barr Virus, e.g., or other methods such as radiological or chemical mutagenesis. The immortalized plasma cells can also be cancerous and can be obtained by injecting mineral oil or another compound, into the peritoneal cavity of an animal.

In one embodiment of the invention, the immortalized fusion partners are what is known in the art as "myeloma cells." Myelomas are generally formed from the fusion of spleen cells with an immortalized fusion partner obtained from an organism suffering from multiple myeloma, a bone marrow cancer. The organism can be birds, fishes, reptiles, mammals and other Animalia. Examples of myeloma cell lines include the SP2/0 (American Type Culture Collection (ATCC), Manasas, Va., CRL-1581), NSO (European Collection of Cell Cultures (ECACC), Salisbury, Wiltshire, UK, ECACC No. 85110503), FO (ATCC CRL-1646), and Ag653 (ATCC CRL-1580) cell lines which were obtained from mice. An example of a myeloma cell line obtained from humans is the U266 cell line (ATTC CRL-TIB-196). Those skilled in the art will recognize other myeloma cell lines.

In one embodiment of the invention the myeloma cells are stably transfected with a DNA molecule. Stably transfected myeloma cells may be generated by methods of transfection, screening and selection well known to those of ordinary skill in the art. DNA sequences used to stably transfect the cells may be randomly integrated into the DNA of a myeloma cell or integrated in a site-specific manner. Such DNA sequences may encode UPR pathway components. Additionally, the stably transfected nucleic acid sequences may insertionally inactivate or delete a UPR component such as a UPR gene or transcriptional control sequence.

In another embodiment of the invention, the cellular secretion rate of a protein is increased by stably transfecting the cell with a nucleic acid sequence encoding a siRNA that targets transcripts of a nucleic acid sequence encoding a UPR pathway component. Such siRNAs may target transcripts of a nucleic acid sequence encoding a CHOP protein. Exemplary CHOP proteins are those having the amino acid sequences shown in SEQ ID NO: 8 or SEQ ID NO: 14. Stable transfection with a nucleic acid sequence encoding a siRNA which targets transcripts of nucleic acid sequences encoding murine CHOP-10 are useful in the methods of the invention. Exemplary murine CHOP-10 gene transcript specific siRNA comprise the nucleotide sequences shown in SEQ ID NO: 15 or SEQ ID NO: 16. Those skilled in the art will recognize other nucleic acids encoding siRNAs that target UPR gene transcripts.

Other cells useful in the methods of the invention include Chinese Hamster Ovary (CHO) cells, insect cells and plant cells.

In another embodiment of the invention, transgenic animals constitutively or inducibly expressing UPR proteins at elevated levels relevant to non-transgenic animals can be produced. Techniques for producing transgenic animals are known in the art.

In the methods of the invention, the cells are cultured. Cells may be cultured in suspension or as adherent cultures. Cells may be cultured in a variety of vessels including, for example, bioreactors, cell bags, culture plates, flasks and other vessels well known to those of ordinary skill in the art. Cells may be cultured in any suitable media including chemically defined media formulations. Ambient conditions suitable for cell culture, such as temperature and atmospheric composition, are also well known to those skilled in the art. Methods for the culture of cells are also well known to those skilled in the art.

The present invention also provides plasma cells with changed cellular secretion rates generated by the methods of the invention. The plasma cells may be generated by modulating the activity of a UPR pathway component with a stably transfected nucleic acid encoding a short interfering RNA. The siRNA may target transcripts of a nucleic acid sequence encoding a UPR pathway component such as a CHOP protein. The plasma cell provided may be, for example, a SP2/0 derived cell such as a C2-8 or C2-18 cell. Such plasma cells may secrete an antibody or other polypeptide to be purified.

The present invention will now be described with reference to the following specific, non-limiting Examples.

EXAMPLE 1

UPR Gene Transcript Levels in High Secreting Cell Lines

Cell lines that secrete mAbs at high rates were analyzed for levels of UPR gene transcripts compared to cell lines secreting an identical mAb at low rates. The cell lines examined included the high secreting lines C505B, C505C and C505D. The low secreting lines examined were the C505A line and SP2/0, the parent myeloma cell line of C505A, B, C and D. All of these lines were transfected with DNA encoding the heavy and light chains of a human IgG1 mAb specific for αv-integrin. The C505B, C505C and C505D cell lines were identified by sequential subcloning, screening and selection for high rates of mAb secretion.

Antibody secretion rates were determined by measuring the amount of mAb secreted in a 24 hour period into the cell culture medium and counting the number of viable cells to generate a cell secretion rate with units of "pg/viable cells/day." The C505a cell line secretes antibody at low rates of 5-7 pg/viable cell/day, equivalent to a concentration of about 5-10 µg/mL/7 days. The C505B line produces antibody at a rate of about 15 pg/viable cell/day, C505C produces at a rate of about 13 pg/viable cell/day, and C505D produces at a rate of about 15 pg/viable cell/day.

All mAb secreting cell lines and the parent myeloma cell line were cultured in suspension at 37° C. in IMDM media containing 5% FBS, 2 mM glutamine, and 2 mM pyruvate in an atmosphere of 5% $CO_2$. 1×MHX selection medium containing 0.5 mg/L mycophenolic acid, 2.5 mg/L hypoxanthine and 50 mg/L xanthine was also present in the media.

Differences in UPR gene transcript levels between the high and low expressing cell lines were assessed via quantitative PCR (Q-PCR). Cells were grown into the exponential growth phase and total RNA was isolated from $5 \times 10^6$ cells using the RNEasy™ system (Qiagen Inc., Valencia, Calif.). Q-PCR was performed using a standard two-step reaction. The cDNA synthesis step was performed using Superscript™ II reverse transcriptase (Invitrogen Inc., Carlsbad, Calif.) and random hexamer primers using reaction conditions specified by the manufacturer. Taqman™ Q-PCR (Applied Biosystems, Foster City, Calif.) was then performed with ABI PRISM™ 7000HT or 7900HT instrumentation (Applied Biosystems, Foster City, Calif.) as specified by the manufacturer. 5,000 pg of RNA was used in each Q-PCR reaction. BiP, CHOP, and XBP specific primers and probe combinations used for Q-PCR were designed using Primer Express™ software (Applied Biosystems, Foster City, Calif.). cDNA levels were normalized against transcript levels for the glyceraldehyde-3-phosphate dehydrogenase (GAPDH) housekeeping gene and then normalized to the cDNA/GAPDH transcript value for the appropriate parent cell line. Data collection and transcript quantitation in the early exponential phase of the PCR was performed using the ABI PRISM 7000HT or 7900HT instrumentation and associated software.

The results are shown in FIG. 1 and show that BiP and XBP-1 UPR gene transcript levels were about 3-4 times greater in high secreting cell lines than in low secreting cells. Differences in CHOP levels were less pronounced.

EXAMPLE 2

UPR Gene Transcript Levels and Antibody Secretion Rates in Static Growth Phase Cells Cells in the static growth phase were analyzed for levels of UPR gene transcripts and mAb secretion rates relative to cells in the exponential growth phase. The C168J cell line is a transfectoma derived from the SP2/0 parent myeloma cell line and secretes IgG1 mAb at a rate of 25-30 pg/cell/day. C505A is as described above in Example 1.

The IgG1 mAb secretion rates of the C505A, C168J, and SP2/0 cell lines were assessed by seeding $5 \times 10^6$ cells in T-75 or T-150 flasks and culturing as described in Example 1. After 3 days cells were in the exponential growth phase and at 6 days cells were in the static growth phase. Total cell number and viable cell number were determined for cells in both growth phases. Culture media from cells in both growth phases was assayed for human IgG by standard enzyme linked immunosorbent assay (ELISA). BiP, CHOP, and XBP-1 specific Q-PCR was performed for exponential and static growth phase cells as described in Example 1 above.

The results shown in Table 1 demonstrate that the C505A and C168j lines have increased IgG1 mAb secretion rates (Table 1).

TABLE 1

| Cell line | Rate of Secreted IgG1 (pg/cell/day) | |
|---|---|---|
| | Exponential Phase | Static Phase |
| C505A | 3.90 | 5.40 |
| C168j | 10.40 | 13.90 |
| SP2/0 | 0 | 0 |

Figure 2:
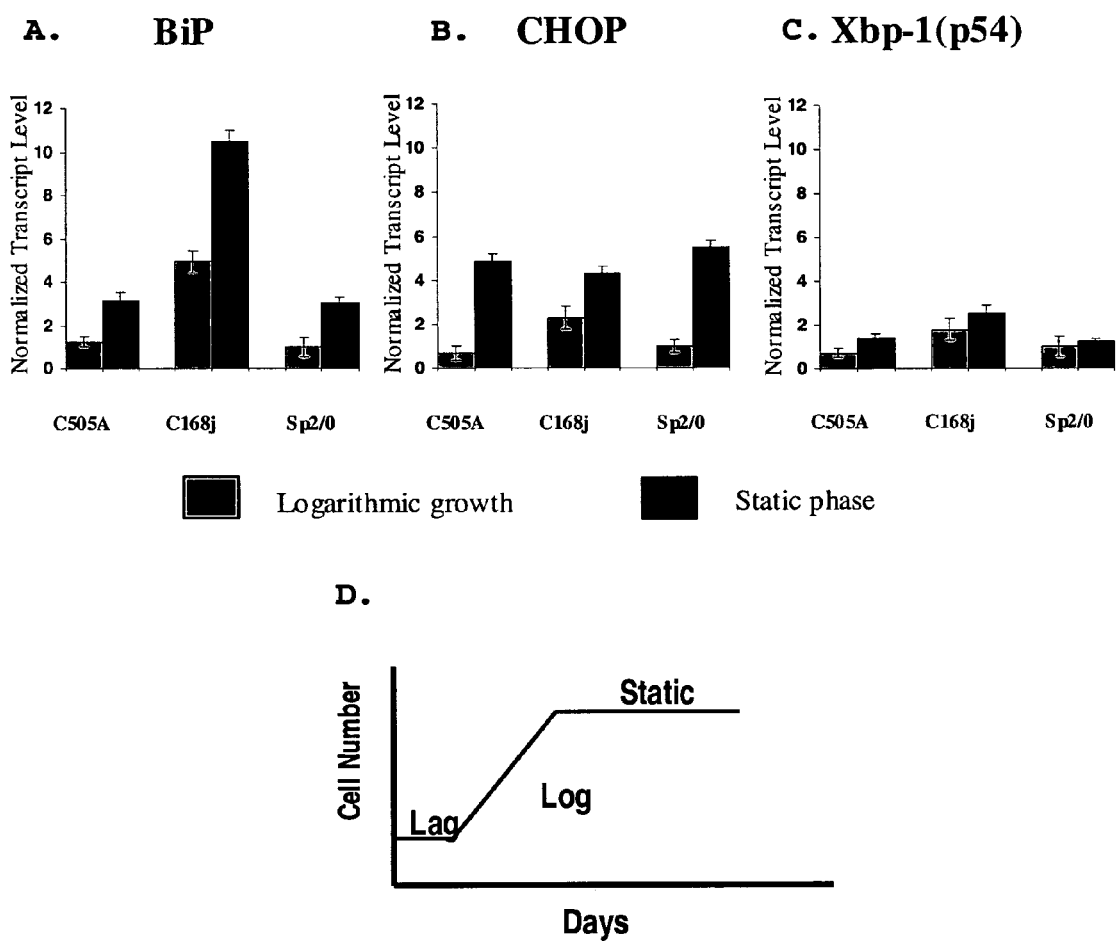
FIG. 2 shows UPR gene transcript levels in static growth phase cells.

Further, the results shown in FIG. 2 demonstrate increased UPR gene transcript levels in C505A, C168j and Sp2/0 in static phase growth relative to exponential phase growth.

EXAMPLE 3

UPR Gene Transcript Levels in Parent Myeloma Cell Lines

Figure 3:
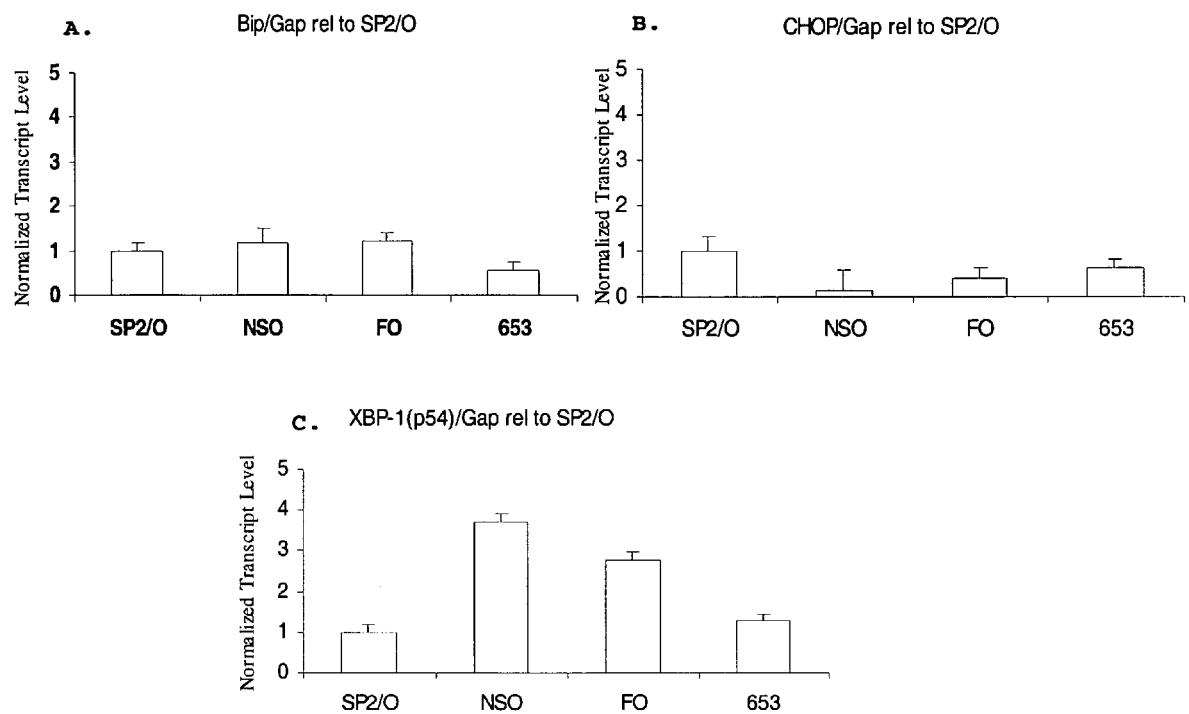
FIG. 3 shows a comparison of UPR gene transcript levels in parent myeloma cell lines.

UPR gene transcript levels in the SP2/0, NSO, FO, and Ag653 parental myeloma cell lines were examined to determine whether higher secreting cell lines contain higher levels of UPR genes. SP2/0, NSO, FO, and Ag653 cells were grown into the exponential growth phase and total RNA was isolated from $5 \times 10^6$ cells as described in Example 1 above. Q-PCR and analysis was also performed as described in Example 1. The results shown in FIG. 3 show comparable BiP and CHOP transcript levels in all cells examined. However, XBP-1 transcript levels were elevated in FO and NSO cells relative to the other cell types examined.

EXAMPLE 4

UPR Gene Transcript Levels in High Secreting Cell Lines and Parent Myeloma Cell Lines Cell lines that secrete mAbs at high rates were analyzed for levels of UPR gene transcripts compared to their parental cell lines. The cell lines indicated in FIGS. 4-6 were grown into the exponential growth phase and total RNA was isolated from $5 \times 10^6$ cells as described in Example 1 above. Q-PCR and analysis was also performed as described in Example 1.

Figure 4:
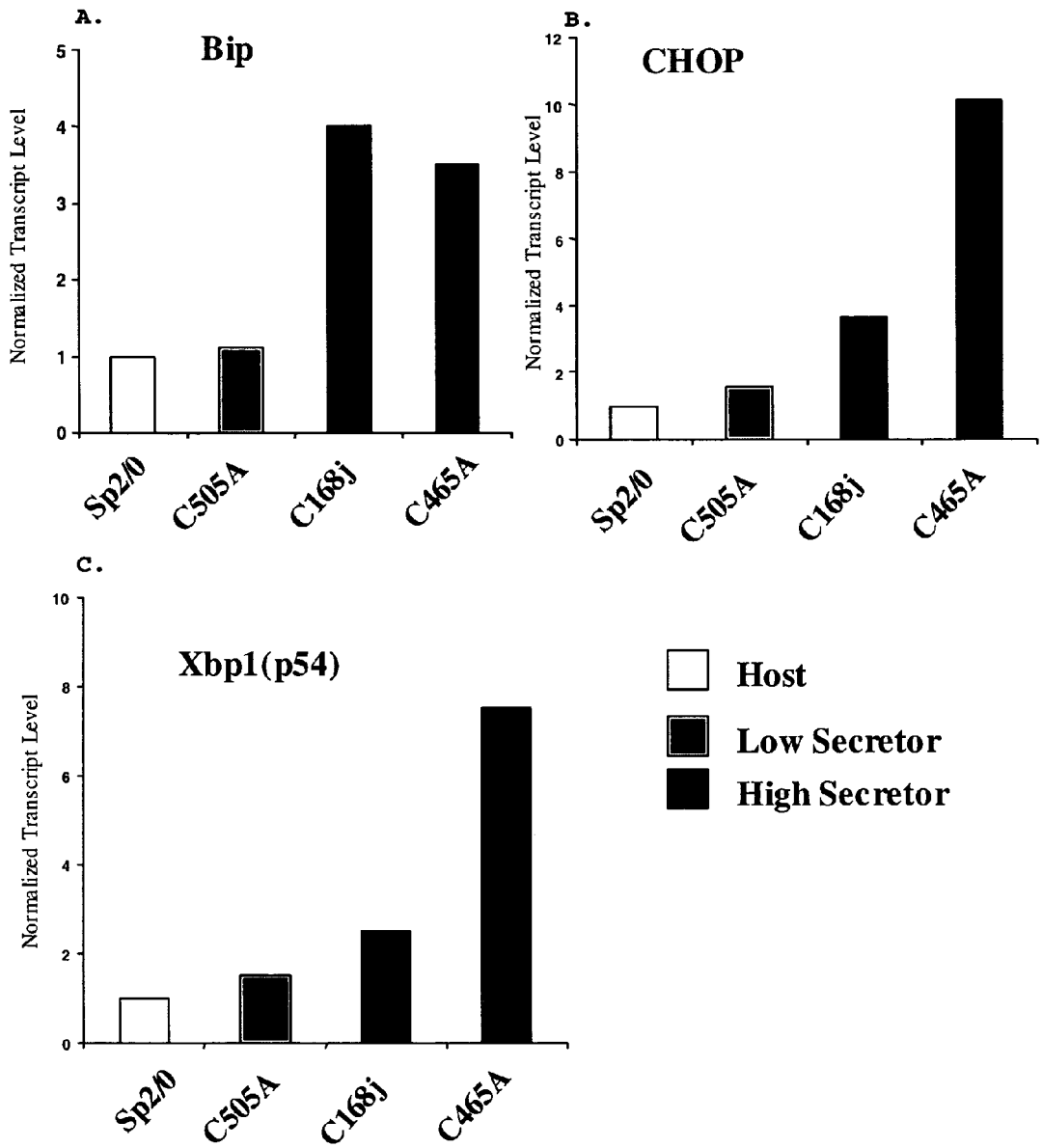
FIG. 4 shows UPR gene transcript levels in high secreting cell lines relative to the Sp2/0 parent myeloma cell line.
Figure 5:
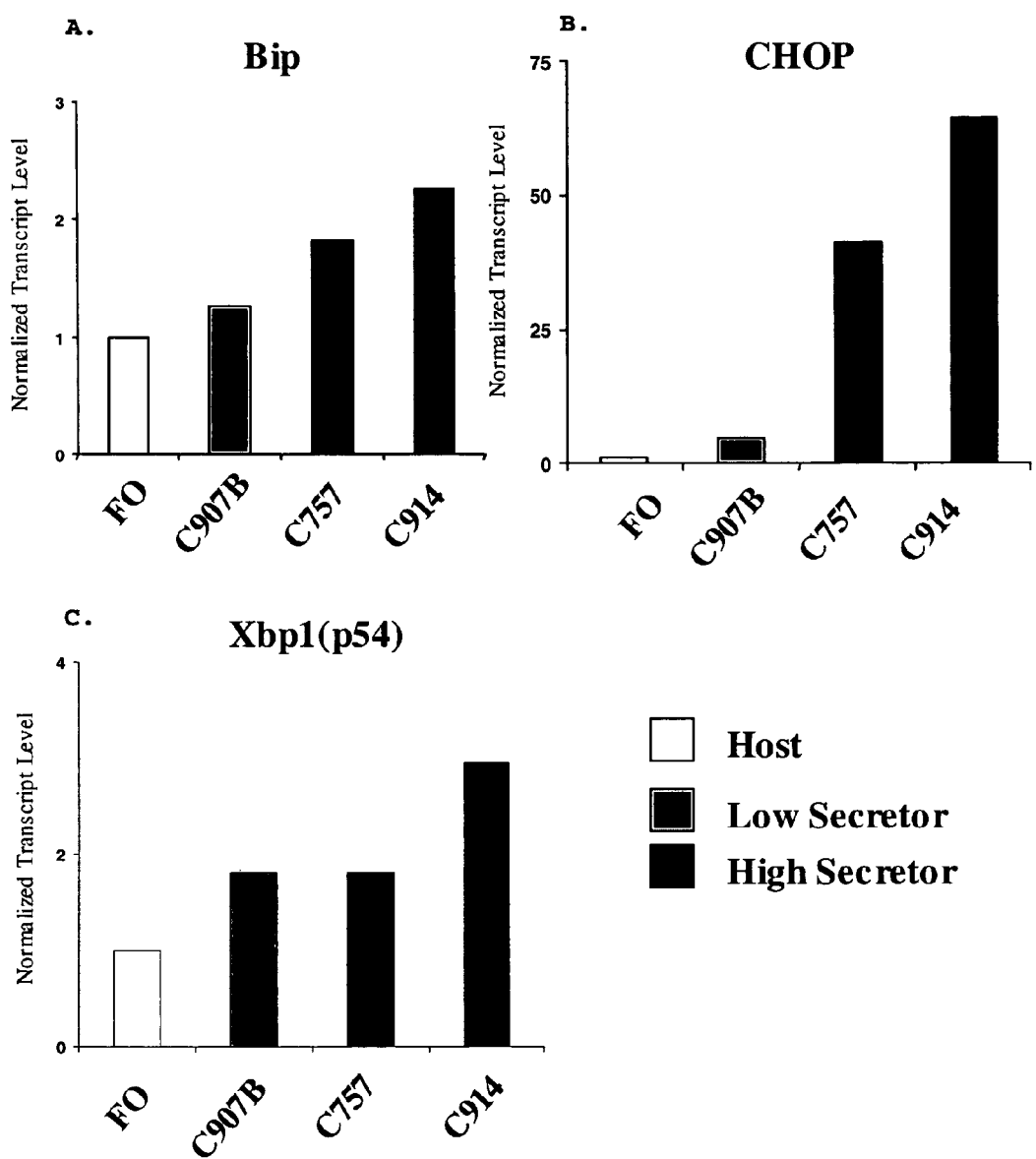
FIG. 5 shows UPR gene transcript levels in high secreting cell lines relative to the FO parent myeloma cell line.
Figure 6:
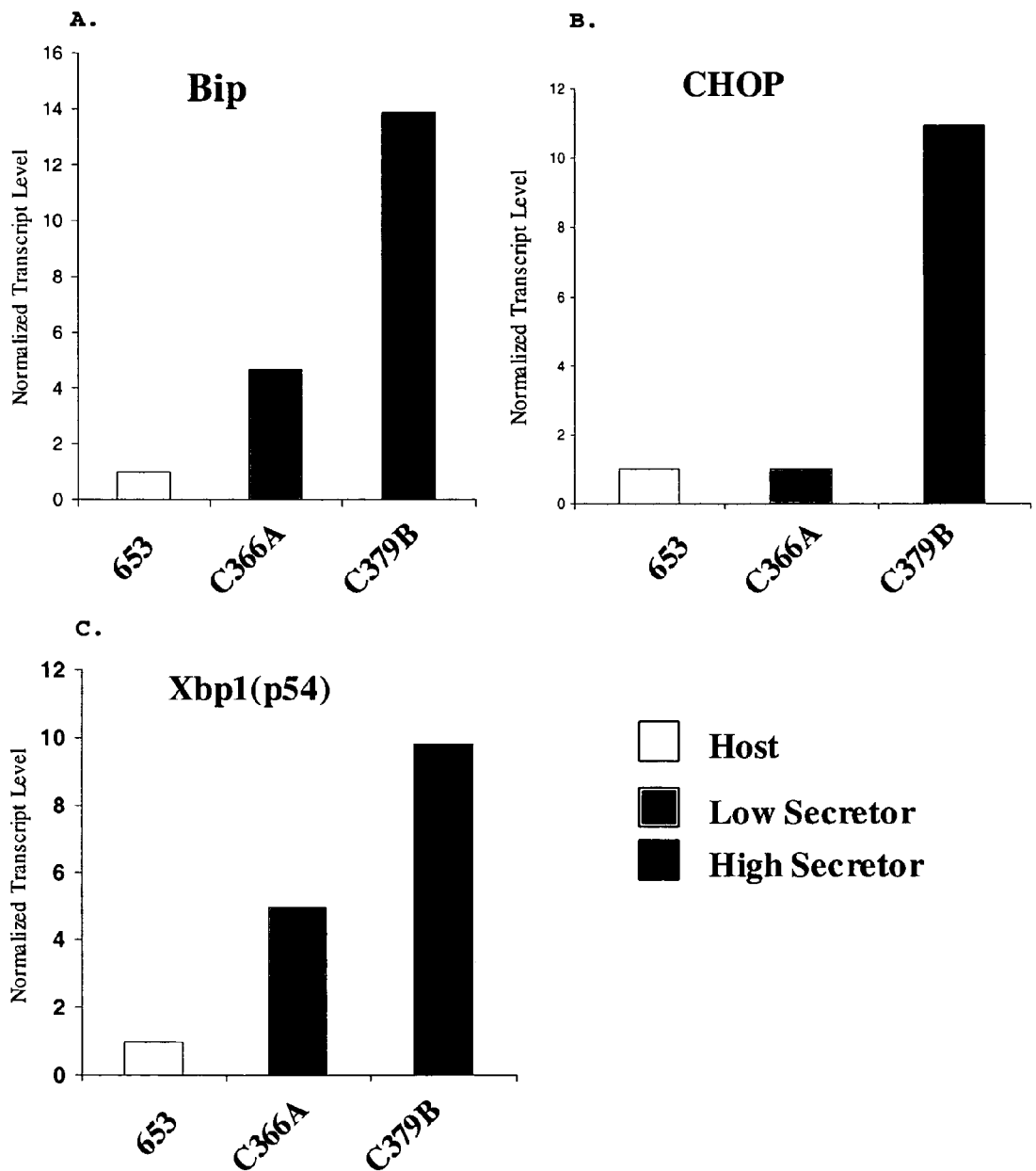
FIG. 6 shows UPR gene transcript levels in high secreting cell lines relative to the Ag-653 parent myeloma cell line.

The results shown in FIGS. 4-6 shows that cell liness secreting mAbs at higher rates have higher UPR gene transcript levels relative to their SP2/0, FO, and Ag653 parent myeloma cell lines. These results suggest that increased UPR gene expression is coupled with increased antibody secretion rates regardless of the identity of the parent myeloma cell line used to generate the high secreting cells.

EXAMPLE 5

UPR Protein Expression After UPR Induction

UPR protein expression in high secreting cells relative to low secreting cells and parent myeloma cell lines were analyzed after UPR induction by the pharmacological agent thapsigargin. Thapsigargin is an ATPase inhibitor that blocks sarcoplasmic endoplasmic reticulum $Ca^{2+}$ ATPase (SERCA) pumps and leads to calcium depletion in the ER lumen.

Cells were treated with 100 nM of thapsigargin and XBP-1 and CHOP-specific Western blots prepared. Cells were lysed at defined timepoints in radioimmunoprecipitation (RIPA)

lysis buffer (1×PBS, 1% N-P40, 0.5% Sodium deoxycholate, 0.1% Sodium dodecylsulfate, 1 mM PMSF, and protease inhibitors from Roche (Catalog No. 1836153) and protein concentrations in the clarified lysates were quantitated using a standard bicinchoninic acid (BCA) protein assay (Sigma Catalog. No. B9643). For Western blots, 20 μg of each lysate was run on a standard SDS-PAGE gel, transferred to polyvinylidene fluoride (PVDF) membranes, and probed with antibodies specific for XBP-1 or CHOP (Santa Cruz Biotechnology Inc., Santa Cruz, Calif.).

The results (not shown) indicated that UPR proteins in high secreting cells are expressed at high levels relative to low secreting cells and parent myeloma cell lines. The XBP-1-specific Western blot indicates that XBP-1 protein expression is strongly induced in thapsigargin treated, high secreting C168j cells. This induction of XBP-1 expression is most pronounced 7 hours after pharmacological induction of the UPR, and is visible as early as 2 hours post-treatment. The CHOP-specific Western blot indicates that CHOP protein expression is strongly induced in thapsigargin treated, high secreting C168j cells. CHOP first appears at 2 hours, is maximally expressed at 4 to 7 hours and is much reduced by 22 hours.

EXAMPLE 6

Increasing UPR Protein Expression Levels

Cells were transiently transfected with BiP and XBP-1 expression vectors in an attempt to elevate cellular expression levels of these UPR proteins. HEK293T/17 (ATCC CRL-11268) cells were grown as adherent cultures at 37° C. in an atmosphere of 5% $CO_2$ and cultured in Iscove's Modified Dubelcco's Minimal Essential Media (IMDM) media containing 5% FBS, 2 mM glutamine, and 2 mM pyruvate. cDNAs encoding XBP-1 isoform 1 (NCBI Accession AF027963), XBP-1 isoform 2 (NCBI Accession AF443192), or BiP were subcloned using standard methods into a vector useful for transient transfection experiments. The vector expresses the zsGreen1 protein under the control of a CMV promoter and has a multiple cloning site for introduction of an additional coding region under the control of a CMV promoter. A kanamycin resistance gene was used for bacterial selection. HEK293T/17 cells were then either left untransfected or transiently transfected with the empty vector alone, XBP-1 isoform 1 expression vector, XBP-1 isoform 2 expression vectors or BiP expression vector. Transfections were performed using the Lipofectamine™ 2000 reagent (Invitrogen Inc., Carlsbad, Calif.) as directed by the manufacturer. Forty-eight hours following transfection the cells were lysed in RIPA lysis buffer and equal cell equivalents of clarified lysates were loaded onto SDS-PAGE gels. Western blots were then prepared and probed as described in Example 5 above. Blots were then stripped and reprobed with an actin-specific antibody to confirm equal protein loading in each lane.

The results (not shown) demonstrated that XBP-1 isoform 1 (lane labeled "XBP-1") and XBP-1 isoform 2 (lane labeled "X54") expression levels were elevated in cells transiently transfected with expression vectors encoding these XBP-1 isoforms. Further, the data (not shown) indicated that BiP expression levels were elevated in cells transiently transfected with expression vectors encoding Bip and in the cells left untransfected or transfected with empty vector alone, no BiP expression was detected.

EXAMPLE 7

Effect of UPR Gene Transcript Levels on Antibody Secretion Rates

The effect of UPR gene transcript levels on antibody secretion rates was analyzed. Double-stranded siRNA molecules targeted to BiP, CHOP, and XBP-1 gene transcripts were designed using Ambion's internet based siRNA Target Finder Tool (www.ambion.com/techlib/misc/siRNA_finder.html) and were synthesized using the Silencer™ siRNA Construction Kit (Ambion Inc., Woodward, Tex., Catalog No. 11620). Two siRNAs were designed for each targeted transcript. $3\times10^6$ C168J cells cultured under standard conditions were transfected via electroporation with 3 μg of each of these double-stranded siRNAs as indicated in FIG. 10. Electroporated cells were suspended in 2 ml of IMDM media as described in Example 1 above and then cultured on T-12 plates. Viable cell concentrations were determined 8 days later. IgG1 mAb concentrations were also determined 8 days later using standard nephelometry techniques.

Figure 7:
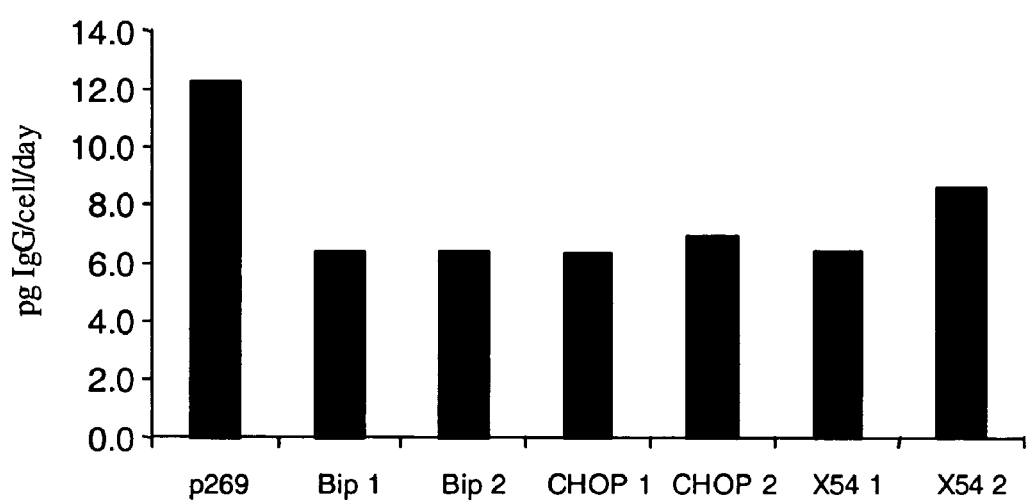
FIG. 7 shows changes in antibody secretion rates as a function of alteration of UPR gene transcript levels.

The results in FIG. 7 show that antibody secretion rates can be modulated by altering UPR gene transcript levels on antibody secretion rates. Transfection of high secreting C168J cells with short interfering RNAs (siRNA) capable of preventing expression of the UPR genes BiP, CHOP, and XBP-1 isoforms from RNA transcripts decreased C168J cell IgG1 secretion rates.

EXAMPLE 8

Increasing Antibody Secretion Rates by Increasing UPR Gene Transcript and Expression Levels Over-expression of UPR proteins can increase the secretion rates of proteins such as mAbs by cells. Protein secreting cell lines, such as mAb secreting cell lines, are transfected with expression vector constructs encoding BiP, CHOP, XBP-1, and other UPR associated proteins to effect the overexpression of these proteins. Cells are transfected with these expression vector constructs either individually or in combination. Appropriate protein secretion rates, such as antibody secretion rates, are determined at 2, 4 and 6 days after transfection using standard techniques. Protein secretion rates in transfected cells are compared to the secretion rates of non-transfected control cells. Protein secretion rates are expected to be higher in cells over-expressing one or more UPR proteins. In the event that constitutive overexpression of Bip or Xbp-1 eventually induces apoptosis in these cells, these genes can be placed downstream of an inducible promoter and activated only when needed.

EXAMPLE 9

Figure 8:
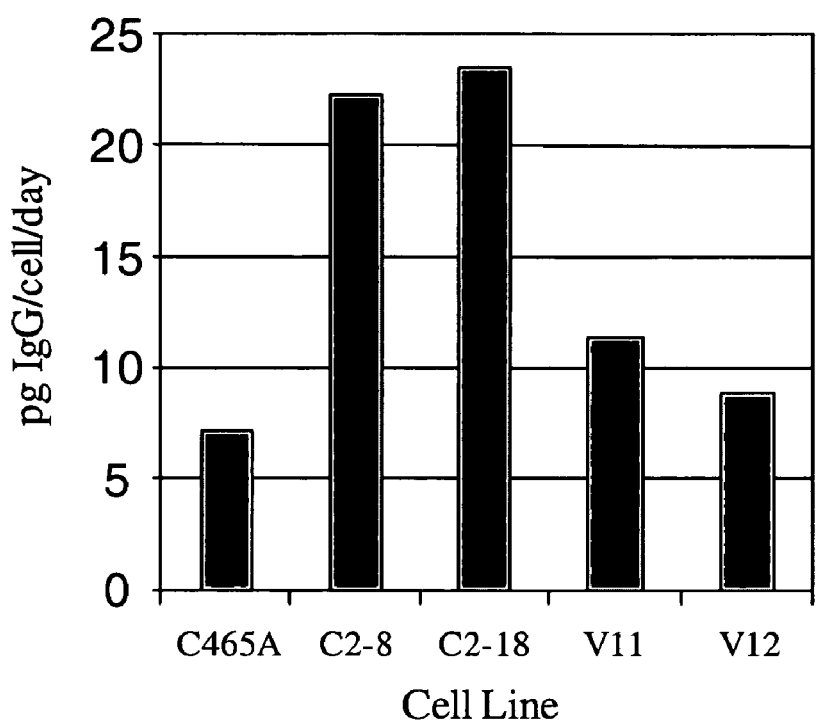
FIG. 8 shows increased antibody secretion rates in myeloma cells stably transfected with nucleic acid encoding CHOP-10 specific siRNAs.

Increasing Antibody Secretion Rates in Myeloma Cells Stably Transfected with CHOP-10 Encoding siRNA Stable transfection of C465A myeloma cells with DNA constructs producing CHOP-10 specific siRNAs increased antibody secretion rates (FIG. 8). Two different siRNA molecules targeted to CHOP-10 gene transcripts were designed using Ambion's internet based siRNA Target Finder Tool (www.ambion.com/techlib/misc/siRNA_finder.html). The siRNA molecules designed were of the short hairpin type. Nucleic acids encoding these siRNAs (SEQ ID NO: 15 and SEQ ID NO: 16) were synthesized and cloned into the BamHI and HindIII sites of the pSILENCER4.1-neo vector (Ambion Inc., Woodward, Tex.) using standard methods. Cloning of the nucleotide sequence shown in SEQ ID NO: 15 into pSILENCER4.1-neo produced pCHOP1, while cloning of the sequences shown in SEQ ID NO: 16 into this vector produced pCHOP2. The pCHOP1, pCHOP2, and pSILENCER4.1-neo plasmid DNAs were then each separately transfected into C465A myeloma cells by electroporation. Stably transfected myeloma cells containing these vectors were then selected in SFM8 media containing 10% FBS and 300 µg/ml G418 by culture at 37° C. in an atmosphere of 5% $CO_2$. This selection media also contained 1×MHX selection medium containing 0.5 mg/L mycophenolic acid, 2.5 mg/L hypoxanthine and 50 mg/L xanthine to maintain stable antibody expression by the C465A cells.

Each cell line indicated in FIG. 8 was grown in suspension for six days in SFM8 media containing 10% FBS, 1×MHX and 300 µg/ml G418. Viable cell density and antibody titers were determined daily during this six day period. Viable cell density was assayed by standard dye exclusion assays and antibody titer in the culture media was assayed by standard nephelometry techniques. The C465A myeloma cell line is derived from the SP2/0 myeloma cell line and stably expresses a human TNF-alpha specific murine mAb of the IgG1 kappa isotype. The C2-8 myeloma cell line is a C465A derived cell line stably transfected with pCHOP1. The C2-18 myeloma cell line is a C465A derived cell line stably transfected with pCHOP2. The V11 and V12 cell lines are C465A derived cell lines stably transfected with pSILENCER4.1-neo alone; both lines were independently generated.

The data obtained indicated that the CHOP-10 specific siRNAs encoded by pCHOP1 and pCHOP2 increased antibody specific productivity relative to the control C465A, V11, and V12 cell lines (FIG. 8).

The present invention now being fully described, it will be apparent to one of ordinary skill in the art that many changes and modifications can be made thereto without departing from the spirit and scope of the appended claims.

The invention claimed is:

1. A method for increasing the cellular secretion rate of a protein comprising the steps of:
   a) decreasing the activity of an unfolded protein response (UPR) pathway component in a cell by stably transfecting the cell with a nucleic acid encoding a siRNA that targets transcripts of a nucleic acid sequence encoding a CHOP protein, wherein the nucleic acid encoding the siRNA is the nucleic acid sequence of SEQ ID NO: 15 or SEQ ID NO: 16; and b) culturing the cells.

2. The method of claim 1 wherein the CHOP protein has the amino acid sequence shown in SEQ ID NO: 8.

3. The method of claim 1 wherein the cell is a myeloma cell.

4. The method of claim 3 wherein the myeloma cell is a SP2/0 cell.

5. The method of claim 3 wherein the myeloma cell is an F0 cell.

6. The method of claim 1 wherein the cell is a Chinese Hamster Ovary (CHO) cell.

* * * * *